(12) United States Patent
Sorger et al.

(10) Patent No.: US 6,924,386 B2
(45) Date of Patent: Aug. 2, 2005

(54) ENANTIOSELECTIVE REFORMATSKY PROCESS FOR PREPARING OPTICALLY ACTIVE ALCOHOLS, AMINES AND DERIVATIVES THEREOF

(75) Inventors: Klas Sorger, München (DE); Hermann Petersen, Burghausen (DE); Jürgen Stohrer, Pullach (DE)

(73) Assignee: Consortium für elektrochemische Industrie GmbH, Munich (DE)

( * ) Notice: Subject to any disclaimer, the term of this patent is extended or adjusted under 35 U.S.C. 154(b) by 155 days.

(21) Appl. No.: 10/639,807

(22) Filed: Aug. 12, 2003

(65) Prior Publication Data

US 2004/0096211 A1 May 20, 2004

(30) Foreign Application Priority Data

Aug. 14, 2002 (DE) .......................................... 102 37 275

(51) Int. Cl.[7] .............................................. C07C 29/10
(52) U.S. Cl. ........................................ 558/303; 568/700
(58) Field of Search .......................... 558/303; 568/700

(56) References Cited

U.S. PATENT DOCUMENTS 6,417,377 B1    7/2002   Pöchlauer et al.

FOREIGN PATENT DOCUMENTS

EP      1223 168    7/2002

OTHER PUBLICATIONS

J.M. Andres, Y. Martin, R. Pedrosa, A. Perez–Encabo, Tetrahedron, 1997, 53, p. 3787.
M. Guetté, J. Capillon, J.P.–Guetté, Tetrahedron, 1973, 29, p. 3659.
D. Seebach, W. Langer, Helvetica, Chimica Acta, 1979, 62, p. 1701.
A. Ojida, T. Yamano, N. Taya, A. Tasaka, Org. Lett. 2002, 4, p. 3051.
Y. Ukaji, S. Takenaka, Y. Horita, K. Inomata, Chem. Lett. 2001, p. 254.
A. Fürstner, Synthesis. 1989, p. 571.
G. Picotin, P. Miginiac, J. Org. Chem., 1987, 52, p. 4796.
Y. Zhang, W. Wu, Tetrhedron, Asymmetry, 1997, 21, 3575–3578.
C. Jiang et al., Huaxue Tongbolo, 2001, 10, 637–640, STN[HCAPLUS]AN: 2001–817298.
R. Pedrosa et al., Tetrahedron, 2000, 56, 1217–23.
Y. Butsugan et al., J. Chem. Soc. Perkin Trans. 1, 1992, 711–713.

Primary Examiner—Taofiq Solola
(74) Attorney, Agent, or Firm—Collard & Roe, P.C.

(57) ABSTRACT

A process is provided for preparing optically active alcohols, amines and derivatives thereof by reacting aldehydes or imines at a temperature of less than 15° C. in the presence of a chiral, enantiomerically pure auxiliary with an organozinc halide which is obtained from zinc and a reactive halogen compound, and water, acid or base, or an alkylating, arylating, acylating or silylating reagent is subsequently added.

10 Claims, No Drawings

ENANTIOSELECTIVE REFORMATSKY PROCESS FOR PREPARING OPTICALLY ACTIVE ALCOHOLS, AMINES AND DERIVATIVES THEREOF

BACKGROUND OF THE INVENTION

1. Field of the Invention

The present invention relates to an enantioselective Reformatsky process for preparing optically active alcohols, amines and derivatives thereof.

2. The Prior Art

The reaction of reactive halogen compounds, in particular α-halo carbonyl compounds, with electrophilic substrates, for example aldehydes, ketones or imines, in the presence of a zinc metal, is known as the Reformatsky reaction. This affords important synthetic building blocks for the preparation of active pharmaceutical ingredients, scents and crop protection agents.

Asymmetric Reformatsky reactions for the targeted preparation of enantiomerically pure synthetic building blocks, for example alcohols and amines, are becoming ever more important.

For example, M. Guette, J. Capillon, J.-P. Guette, Tetrahedron, 1973, 29, p. 3659 disclose an enantioselective Reformatsky synthesis of (S)-(-)-3-hydroxy-3-phenylpropionic esters using benzaldehyde as the substrate in the presence of the chiral ligand (-)-sparteine in the relatively noncoordinating solvents benzene and dimethoxymethane. Although the process provides high enantioselectivities of up to 95±3% ee, only very low chemical yields of a maximum of 38 i 7% of theory could be achieved.

Pedrosa et al. (J. M. Andres, Y. Martin, R. Pedrosa, A. P,rez-Encabo, Tetrahedron, 1997, 53, p. 3787) describe an enantioselective Reformatsky reaction for preparing optically active β-hydroxy esters using amino alcohols as chiral auxiliaries in tetrahydrofuran.

However, high chemical yields of up to 90% are achieved at only moderate enantioselectivities of from 22 to 62% ee. In addition, the process is based on the use of large excesses of the organozinc compound (Reformatsky reagent) and is therefore of little interest from an economic and industrial point of view.

Seebach et al. (D. Seebach, W. Langer, Helv. Chim. Acta 1979, 62, p. 1701) describe an enantioselective Reformatsky reaction using chiral diamines as cosolvents with good chemical yields of up to 95%, but only small enantiomeric excesses of a maximum of 24.5% ee.

Ojida et al. (A. Ojida, T. Yamano, N. Taya, A. Tasaka, Org. Lett. 2002, 4, p. 3051) describe an enantioselective Reformatsky process using cinchona amino alcohols as chiral ligands and ketones as substrates. High enantioselectivities (up to 97% ee) could only be achieved where an $sp^2$ nitrogen atom adjacent to the carbonyl group of the ketone substrate makes chelation of the zinc possible. Other ketone substrates and aldehydes as electrophilic substrates deliver only moderate optical yields of 15–70% ee. In addition, the process requires a large excess of Reformatsky reagent and expensive pyridine as a basic assistant, which means that the process is of little interest from an economic and industrial point of view.

Ukaji et al. (Y. Ukaji, S. Takenaka, Y. Horita, K. Inomata, Chem. Lett. 2001, p. 254) describe an enantioselective Reformatsky process for preparing optically active β-amino acid esters using diisopropyl tartrate as a chiral auxiliary. Even though enantioselectivities of up to 98% ee and yields of up to 80% could be achieved, the process requires the use of large excesses both of the organozinc compound (diethylzinc) and of very expensive iodoacetic ester. This process is therefore unsuitable for preparing optically active β-amino acid esters from an economic and industrial point of view.

None of the existing processes delivers both high chemical and high optical yields while economically using reagents used, in particular organozinc compounds. The prior art processes are therefore unsuitable in particular for economic and industrial scale synthesis of optically active alcohols and amines.

SUMMARY OF THE INVENTION

It is therefore an object of the invention to provide an economical, enantioselective Reformatsky process which can be carried out universally and on the industrial scale and, in an enantioselective synthesis, leads to highly enantiomerically enriched alcohols and amines or derivatives thereof in high yields and solves the problems known from the prior art.

It has been found that, surprisingly, the preparation of optically active alcohols and amines and derivatives thereof may be carried out particularly advantageously and economically in the form of an enantioselective Reformatsky reaction using chiral, enantiomerically pure auxiliaries having at least two nitrogen donors and at least one cyclic group (N-auxiliary), and using a multiplicity of substrates.

The invention therefore provides a process for preparing compounds of the general formula (1a) or (1b)

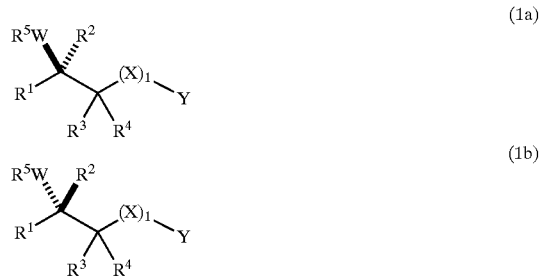

where
$R^1$ and $R^2$ are each independently hydrogen or an optionally halogen- or cyano-substituted $C_1$–$C_{30}$-hydrocarbon radical in which one or more, nonadjacent methylene units may be replaced by —O—, —CO—, —COO—, —OCO—, or —OCOO—, —S— or —NR$^x$— groups, and in which one or more methine units may be replaced by —N= or —P= groups, $R^3$ and $R^4$ are each independently hydrogen, halogen, or an optionally halogen-substituted or cyano-substituted $C_1$–$C_{30}$-hydrocarbon radical in which one or more, nonadjacent methylene units may be replaced by —O—, —CO—, —COO—, —OCO—, or —OCOO—, —S— or —NR$^x$— groups, and in which one or more methine units may be replaced by —N= or —P= groups, $R^x$ is hydrogen or an optionally halogen-substituted $C_1$–$C_{30}$-hydrocarbon radical in which one or more, nonadjacent methylene units may be replaced by —O—, —CO—, —COO—, —OCO—, or —OCOO—, —S—, —NH— or —N—$C_1$–$C_{20}$-alkyl groups, and in which one or more methine units may be replaced by —N= or —P= groups, and X is selected from

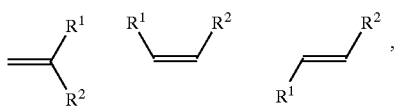

l is an integer having the value 0 or 1,

W may be O or $NR^6$, $R^5$ may be hydrogen or an alkyl, aryl, acyl or silyl group and $R^6$ may be hydrogen, $Si(R^1)_3$ or an optionally halogen- or cyano-substituted $C_1$–$C_{30}$-hydrocarbon radical in which one or more, nonadjacent methylene units may be replaced by —O—, —CO—, —COO—, —OCO—, or —OCOO—, —S—, —SO—, —SO$_2$—, —P($R^1$)—, —P(O$R^1$)—, —PO($R^1$)—, —PO(O$R^1$)—, or —$NR^x$— groups, and in which one or more methine units may be replaced by —N= or —P= groups, Y is CN, (C=O)—Z, (SO$_2$)—Z, (P=O) (—Z)$_2$ or an aromatic radical where one or more methine units in the ring may be replaced by —N= or —P= groups and the ring may be of the heteroatoms —O—, —S— or —NH—, and where the aromatic ring is optionally halogen- or cyano-substituted or substituted by $C_1$–$C_{30}$-hydrocarbon radicals in which one or more, nonadjacent methylene units may be replaced by —O—, —CO—, —COO—, —OCO—, or —OCOO—, —S— or —NRx- groups, and Z is an optionally halogen-substituted $C_1$–$C_{30}$-hydrocarbon radical in which one or more, nonadjacent methylene units may be replaced by —O—, —CO—, —COO—, —OCO—, or —OCOO—, —S—, or —$NR^x$ groups, and in which one or more methine units may be replaced by —N= or —P= groups, or is OH, $OR^1$, $OSi(R^1)_3$, $NHR^1$ or $NR^1R^2$, which comprises reacting aldehydes or imines of the general formula (2)

at a temperature of less than 15° C.

in the presence of a chiral, enantiomerically pure auxiliary having at least two nitrogen donors and at least one cyclic group, with the proviso that protons present have a pKa of greater than 18 with an organozinc halide which is obtained from zinc and a reactive halogen compound of the general formula (3)

where

Hal is chlorine, bromine or iodine, and subsequently adding water, acid or base, or an alkylating, arylating, acylating or silylating reagent.

The step of the process according to the invention which is synthetically particularly valuable is the efficient construction of a chiral center in high yields in the course of a Reformatsky reaction with high enantiomeric excesses in the β-position by using a chiral enantiomerically pure auxiliary having at least two nitrogen donors and at least one cyclic group, with the proviso that protons present have a pKa of greater than 18 (N-auxiliary).

In view of the reaction conditions during the Reformatsky reaction and in this case especially owing to the addition of zinc, the chiral, enantiomerically pure compounds having at least two nitrogen donors used as chiral N-auxiliaries in the process according to the invention must not have any acidic protons, in particular those having a pKa of less than or equal to 18, for example in the form of free amide functions, such as NH—C=O or NH—SO$_2$, or hydroxyl functions. This makes the chiral auxiliary inert and stable under the reaction conditions of the Reformatsky reaction, in particular toward the Reformatsky reagent. As a consequence, the large excesses of Reformatsky reagent often used in the prior art in particular may be dispensed with.

Particularly preferred N-auxiliaries contain no acidic protons having a pKa of less than or equal to 20.

The nitrogen donors of the N-auxiliary coordinate to the zinc atoms and complex the Reformatsky reagent (organozinc halide), even in the presence of polar and/or coordinating solvents. The resulting chiral Reformatsky reagent differentiates between the re-side and si-side of the aldehyde or imine substrate, which leads to the formation of enantiomerically enriched products. The presence of at least one cyclic group (cycle) in the N-auxiliary limits the flexibility of the transition state as the chiral Reformatsky reagent approaches the re- or si-side of the aldehyde or imine substrate. Thus it increases the selectivity of the reaction, which leads to high optical yields (enantioselectivities) and therefore highly enantiomerically enriched products.

For example, when the open-chain diamine containing no cyclic groups (+)-1,4-dimethylamino-2,3-dimethoxybutane is used as a chiral auxiliary in the process described by Seebach et al. (D. Seebach, W. Langer, *Helv. Chim. Acta* 1979, 62, p. 1701) only small enantiomeric excesses of a maximum of 24.5% ee are achieved.

Typically, the nitrogen donors in the N-auxiliaries used in the process according to the invention are-heteroaromatics, amine, imine or enamine groups.

Preference is given to N-auxiliaries having at least two secondary and/or tertiary amine groups and containing at least one cycle.

Preference is given in particular to chiral, enantiomerically pure diamine compounds containing at least one cycle as auxiliaries, and very particular preference is given to diamine compounds having secondary and/or tertiary amine groups and containing at least one cyclic group.

Very particularly preferred N-auxiliaries are diamine compounds having secondary and/or tertiary amine groups, of which at least one amine group is part of a cycle. A particularly preferred embodiment of the amino auxiliary is (−)-sparteine.

The use of (−)-sparteine generally allows high enantiomeric excesses of the optically active alcohols and amines and derivatives thereof of the general formula (1a) or (1b) to be achieved.

Depending on the structure of the substrate and of the Reformatsky reagent, on the presence of further functional groups, on the solvent used, on the temperature and on any further reaction parameters, the R- or the S-derivative of the optically active product may be prepared, and one handedness (the R- or S-form) is obtained in a targeted manner with a high enantiomeric excess for a certain substrate.

The advantages of the process according to the invention are that the synthesis of optically active alcohols, amines and derivatives thereof can be carried out particularly economically and efficiently, especially when carried out on the industrial scale. This is because the products may be prepared enantioselectively in high yields at simultaneously high purities and high optical purities (enantiomeric excesses) with regard to the 3-oxy- or 3-amino-position in the products of the general formula (1a) or (1b).

In addition, the optically active alcohols, amines and derivatives thereof are prepared using very small excesses of the organozinc halide (Reformatsky reagent). The process is therefore particularly economical from an industrial point of view.

Furthermore, the products can be obtained inexpensively in the process according to the invention within very short reaction times and with very good space-time yields.

The chiral, enantiomerically pure N-auxiliary used can also be recovered in high yields in a very simple manner when working up the reaction mixture and isolating the products and reused. This makes the process according to the invention particularly cost-effective and economical, especially when carried out on the industrial scale.

In the course of the reaction, the addition of water, acid or base, or of an alkylating, arylating, acylating or silylating reagent results in the precipitation of a zinc-containing solid containing the N-auxiliary.

After the precipitate is removed, the N-auxiliary can be recovered from the zinc-containing solid by heating a suspension of the solid in a solvent in the presence of a hydroxide or oxide base. The N-auxiliary is released by this procedure to form sparingly soluble basic zinc salts. After filtration, the N-auxiliary is recovered by removing the solvent and may be advantageously recycled back into the process.

For example, (−)-sparteine can be recovered in a very high yield of >90% when working up the reaction mixture and isolating the products, and reused.

The $C_1$–$C_{30}$-hydrocarbon radicals for $R^1$, $R^2$, $R^3$ and $R^4$ are preferably linear, branched or cyclic $C_2$–$C_{20}$-alkyl, $C_2$–$C_{20}$-alkenyl, $C_5$–$C_{20}$-acetalalkenyl or $C_3$–$C_{20}$-alkoxycarbonylalkyl radicals, each of which may be substituted by F, Cl, Br, I, CN and $C_1$–$C_{10}$-alkoxy radicals and also $C_1$–$C_{10}$-alkylamino radicals, and in which methylene units may be replaced by —O—, —S— or —NR$^x$—, or are each aryl, aralkyl, alkaryl, aralkenyl or alkenylaryl radicals, in each of which one or more methine units may be replaced by —N= or —P= groups, and in which methylene units may be replaced by —O—, —S— or —NR$^x$—, and each of which may be substituted by F, Cl, Br, I, CN, $C_1$–$C_{10}$-alkoxy radicals, $C_1$–$C_{10}$-alkylamino radicals and $C_1$–$C_{10}$-alkyl radicals, and may bear, in the ring, the heteroatoms O—, —S— or —NR$^x$—.

Particularly preferred $R^1$ and $R^2$ radicals are hydrogen, methyl, ethyl, propyl, isopropyl, butyl, sec-butyl, tert-butyl, vinyl, phenyl; amino-, N,N-dimethylamino-, N-acetylamino-, N-acetyl-N-methylamino-, N-benzyloxycarbonylamino-, tert-butyloxycarbonylamino-, nitro-, methyl-, ethyl-, propyl-, isopropyl-, butyl-, sec-butyl-, tert-butyl-, methoxy-, ethoxy-, acetoxy-, benzyloxy-, fluoro-chloro-, bromo-, iodo-, cyanophenyl; benzyl, pyridyl, piperidinyl, thiophene, furan, pyrrole, in particular hydrogen, methyl, ethyl, phenyl and thiophene.

Particularly preferred $R^3$ and $R^4$ radicals are hydrogen, fluorine, chlorine, bromine or iodine, methyl, ethyl, propyl, butyl, tert-butyl, vinyl, phenyl; amino-, N,N-dimethylamino-, N-acetylamino-, N-acetyl-N-methylamino-, N-benzyloxycarbonylamino-, tert-butyloxycarbonylamino-, nitro-, methyl-, ethyl-, propyl-, isopropyl-, butyl-, sec-butyl-, tert-butyl-, methoxy-, ethoxy-, acetoxy-, benzyloxy-, fluoro-chloro-, bromo-, iodo-, cyanophenyl; benzyl, pyridyl, piperidinyl, thiophene, furan and pyrrole, in particular hydrogen, fluorine, chlorine, methyl and phenyl.

Preferred $R^5$ radicals are hydrogen, Si(R$^1$)$_3$ where R$^1$ is in particular selected from the preferred embodiments of $R^1$ or is linear, branched or cyclic $C_1$–$C_{20}$-alkyl, $C_2$–$C_{20}$-alkenyl, $C_5$–$C_{20}$-acetalalkenyl or $C_3$–$C_{20}$-alkoxycarbonylalkyl radi-cals which may be substituted by F, Cl, Br, I, CN and $C_1$–$C_{10}$-alkoxy radicals and also $C_1$–$C_{10}$-alkylamino radicals, and in which methylene units may be replaced by —O—, —S— or —NR$^x$—, or aryl, aralkyl, alkaryl, aralkenyl or alkenylaryl radicals, in each of which one or more methine units may be replaced by —N= or —P= groups, and in which methylene units may be replaced by —O—, —S— or —NR$^x$— and each of which may be substituted by F, Cl, Br, I, CN, $C_1$–$C_{10}$-alkoxy radicals, $C_1$–$C_{10}$-alkylamino radicals and $C_1$–$C_{10}$-alkyl radicals, and may bear, in the ring, the heteroatoms O—, —S— or —NR$^x$—.

Particularly preferred radicals for $R^5$ are hydrogen, acetyl, propionyl, benzoyl, methyl, ethyl, propyl, butyl, phenyl, benzyl, naphtyl, trimethylsilyl, triethylsilyl, tripropylsilyl, tributylsilyl or butyldimethylsilyl, in particular hydrogen, acetyl, methyl, naphtyl or trimethylsilyl.

Preferred Si(R$^1$)$_3$ radicals for $R^6$ are those in which R$^1$ is selected from the preferred embodiments of $R^1$.

The $C_1$–$C_{30}$-hydrocarbon radicals for $R^6$ are preferably linear, branched or cyclic $C_1$–$C_{20}$-alkyl, $C_2$–$C_{20}$-alkenyl, $C_5$–$C_{20}$-acetalalkenyl or $C_3$–$C_{20}$-alkoxycarbonylalkyl radicals, each of which may be substituted by F, Cl, Br, I, CN or aryl, aralkyl, alkaryl, aralkenyl, alkenylaryl radicals, in each of which one or more methine units may be replaced by —N= or —P= groups, and methylene units may be replaced by —O—, —S—, —NH—.

Particularly preferred $R^6$ radicals are hydrogen, acetyl, benzyloxycarbonyl, tert-butyloxycarbonyl, diphenylphosphinoyl, phenylsulfinyl, tolylsulfinyl, methyl, ethyl, propyl, butyl, phenyl, benzyl, naphthyl, trimethylsilyl, triethylsilyl, tripropylsilyl, tributylsilyl or butyldimethylsilyl, in particular hydrogen, acetyl, methyl, ethyl, benzyloxycarbonyl, tert-butyloxycarbonyl, diphenylphosphinoyl, tolylsulfinyl or trimethylsilyl.

Preferred radicals for $R^x$ are linear, branched or cyclic $C_1$–$C_{20}$-alkyl, $C_2$–$C_{20}$-alkenyl, $C_5$–$C_{20}$-acetalalkenyl or $C_3$–$C_{20}$-alkoxycarbonylalkyl radicals, each of which may be substituted by F, Cl, Br, I, CN and $C_1$–$C_{10}$-alkoxy radicals and also $C_1$–$C_{10}$-alkylamino radicals, and in each of which methylene units may be replaced by —O—, —S— or —NH—, or aryl, aralkyl, alkaryl, aralkenyl or alkenylaryl radicals, in each of which one or more methine units may be replaced by —N= or —P= groups, and in which methylene units may be replaced by —O—, —S—, —NH—, and each of which may be substituted by F, Cl, Br, I, CN, $C_1$–$C_{10}$-alkoxy radicals and $C_1$–$C_{10}$-alkylamino radicals and by $C_1$–$C_{10}$-alkyl radicals, and may bear, in the ring, the heteroatoms O—, —S— or —NH—.

Particularly preferred radicals for $R^x$ are hydrogen, methyl, ethyl, propyl, butyl, tert-butyl, phenyl and benzyl, in particular hydrogen and methyl.

The reactive halogen compounds of the general formula (3) used are preferably reactive α-haloacetic acid derivatives.

Preference is given to reactive α-haloacetic acid derivatives of the general formula (3) where Y is CN or (C=O)—Z and Z is OR$^1$ or OSi(R$^1$)$_3$, and R$^1$ is in particular selected from the above-described preferred embodiments.

Very particularly preferred α-haloacetic acid derivatives of the general formula (3) are α-haloacetonitrile, methyl α-haloacetate, ethyl α-haloacetate and trimethylsilyl α-haloacetate.

Useful reactive halogen compounds of the general formula (3) are in particular chlorine or bromine compounds where Hal is bromine or chlorine, most preferably bromine compounds where Hal is bromine.

Particularly preferred embodiments of reactive halogen compounds are α-bromoacetic esters.

Possible embodiments of reactive bromine compounds are also reaction products of α-haloacetic acid derivatives with silanes, for example compounds of the type [Br—CH$_2$(C=O)—O]$_2$Si(R$^1$)$_2$ or [Br—CH$_2$(C=O)—OSi(R$^1$)$_2$—CH$_2$]$_2$ where R$^1$ is as defined above, in particular the above-described preferred embodiments. The Reformatsky reagents are then obtained from these by reaction with zinc.

In one possible embodiment of the process according to the invention, the first reaction step to obtain the chiral Reformatsky reagent comprises first initially charging zinc in a solvent or solvent mixture and then adding a mixture, optionally dissolved in a solvent, of the reactive halogen compound and the N-auxiliary.

Preference is given to first initially charging zinc and the N-auxiliary in a solvent or solvent mixture and subsequently adding the reactive halogen compound, optionally dissolved in a solvent, to form an organozinc halide of the general formula (3) where Hal in this case means halozinc (organozinc halide).

Particular preference is given to first initially charging zinc in a solvent or solvent mixture and subsequently adding the reactive halogen compound, optionally dissolved in a solvent, to form an organozinc halide. The N-auxiliary is then added to this mixture, optionally dissolved in a solvent.

The reaction is carried out in the presence of a solvent which is inert under the reaction conditions and is added before or after the addition of zinc or the chiral auxiliary or other reagents or additives or optionally together with zinc or the chiral auxiliary or other reagents or additives.

Useful solvents for the process according to the invention are all inert solvents suitable for the Reformatsky reaction. An example of a summary of suitable solvents is contained in A. Furstner, *Synthesis* 1989, p. 571.

Suitable solvents are diethyl ether, dipropyl ether, dibutyl ether, diisopropyl ether, methyl tert-butyl ether, dimethoxymethane, diethoxymethane, dimethoxyethane, diethoxyethane, diethylene glycol dimethyl ether, diethylene glycol diethyl ether, diethylene glycol dipropyl ether, diethylene glycol dibutyl ether, triethylene glycol dimethyl ether, triethylene glycol diethyl ether, triethylene glycol dibutyl ether, methylene chloride and also mixtures of the aforementioned compounds and mixtures of the aforementioned compounds with the solvents benzene, toluene, ethylbenzene, propylbenzene, isopropylbenzene, butylbenzene, xylene, xylene isomer mixture, trimethylbenzene, pentane, hexane, octane, isooctane, nonane, nonane fraction, cyclohexane, cycloheptane, cyclooctane, dimethylcyclohexane, ethylcyclohexane, propylcyclohexane, butylcyclohexane, petroleum and paraffin.

In a preferred embodiment, solvents or cosolvents which coordinate to the zinc or chelate the zinc are used.

Preferred solvents for carrying out the enantioselective Reformatsky reaction according to the invention are those selected from the group of the cyclic ethers, di- or oligoethers having at least one ethylene bridge (glyme compounds), carboxylic esters, amines, amides, polar aprotic solvents or halogenated hydrocarbons or mixtures thereof.

The aforementioned solvents may be used in the process according to the invention as the sole solvent, as an additive to the reaction mixture or in a mixture with one or more inert solvents or solvent mixtures suitable for Reformatsky reactions as cosolvents.

Solvents selected from the group of cyclic ethers, di- or oligoethers having at least one ethylene bridge (glyme compounds), carboxylic esters, amines, amides, polar aprotic solvents or halogenated hydrocarbons or solvent mixtures comprising one or more of these solvents can be used to achieve very high yields of up to >95% and at the same time high enantioselectivities of up to 95%, at simultaneously short reaction times and consequently high space-time yields.

Particularly preferred solvents from the group of ethers, di- and oligoethers having at least one ethylene bridge glyme compounds) are tetrahydrofuran, 2-methyltetrahydrofuran, 2,5-dimethyltetrahydrofuran, 2,5-dimethoxytetrahydrofuran or 1,4-dioxane, dimethoxyethane, diethoxyethane, diethylene glycol dimethyl ether, diethylene glycol diethyl ether, diethylene glycol dipropyl ether, diethylene glycol dibutyl ether, triethylene glycol dimethyl ether, triethylene glycol diethyl ether or triethylene glycol dibutyl ether or mixtures thereof.

Preference is given in particular to using tetrahydrofuran, 2-methyltetrahydrofuran, 2,5-dimethyltetrahydrofuran, 2,5-dimethoxytetrahydrofuran or 1,4-dioxane or mixtures thereof, and very particular preference is given to using tetrahydrofuran or 1,4-dioxane.

Particularly preferred solvents from the group of carboxylic esters, amines, amides, ketones, polar aprotic solvents or halogenated hydrocarbons are methyl, ethyl, n-propyl, isopropyl, n-butyl, isobutyl, t-butyl, n-hexyl, n-pentyl or isopentyl acetate, propionate and butyrate, 2-ethoxyethyl 2-acetate, pyridine, N-acetylpyrrolidine, N-acetylpyrrole, N-acetylsuccinimide, tetramethylurea, N,N'-dimethylethyleneurea, tetramethylguanidine, acetone, methyl ethyl ketone, diethyl ketone, isopropyl methyl ketone, isopropyl ethyl ketone, acetonitrile, propionitrile, butyronitrile, dimethylformamide, diethylformamide, dimethylacetamide, diethylacetamide, 1-methyl-2-pyrrolidone, dimethyl sulfoxide or methylene chloride or mixtures thereof.

Very particularly preferred solvents for the process according to the invention are dimethylformamide, 1-methyl-2-pyrrolidone or tetrahydrofuran or mixtures thereof, in particular tetrahydrofuran or mixtures comprising tetrahydrofuran or other polar solvents.

The organozinc halides of the general formula (3) prepared where Hal is in this case halozinc (organozinc halides) may, optionally also after the addition of the chiral N-auxiliary, initially be stored stably and optionally reacted at a later juncture. They are valuable reagents which are outstandingly suitable for the enantioselective Reformatsky reaction.

During the addition of the reactive halogen compound of the general formula (3) and optionally the chiral N-auxiliary, preference is given to maintaining the temperature of the exothermic reaction at a predetermined value, optionally by cooling. The upper temperature limit may be determined by the boiling point of the solvent used, for example tetrahydrofuran (b.p.: 66° C.) or ethyl acetate (b.p.: 78° C.). In the case of relatively high-boiling solvents, for example 1,4-dioxane (b.p.: 100–102° C.), the temperature of the reaction is preferably controlled by cooling.

The preparation of the organozinc halides is preferably carried out at temperatures of from −20 to +15° C., more preferably from 0 to 100° C., in particular from 25 to 60° C., optionally under reflux and optionally under reduced pressure.

In a particularly preferred embodiment of the process according to the invention, the preparation of the organozinc halides with reflux is carried out between 25 and 50° C. In this way, particularly high product yields and product purities may be achieved.

During the addition of the chiral N-auxiliary to the organozinc halides, the temperature of the exothermic reaction is preferably maintained at a predetermined value, optionally by cooling. The addition is preferably effected at temperatures of from −80 to +100° C., more preferably from −50 to +60° C., in particular from −30 to +30° C.

An aldehyde or imine of the general formula (2) is then added, optionally dissolved in a solvent, to the mixtures of organozinc halides and the chiral N-auxiliary obtained.

Alternatively, the mixtures of the organozinc halides and the chiral N-auxiliary obtained may also conversely be added to aldehydes or imines of the general formula (2), optionally dissolved in a solvent.

It is also possible to add a mixture of aldehyde or imine of the general formula (2) and the chiral N-auxiliary to the organozinc halides or conversely to add the organozinc halides to a mixture of the aldehydes or imines of the general formula (2) and the chiral N-auxiliary.

In the process according to the invention, the organozinc halides in the presence of the enantiomerically pure, chiral N-auxiliary are reacted with the electrophiles selected from the group of aldehydes or imines at a temperature of below 15° C.

It has been found that, surprisingly, only at a temperature of below 15° C. could high product yields and at the same time high chemical and optical purities be achieved.

Guette et al. (M. Guette, J. Capillon, J.-P. Guette, *Tetrahedron*, 1973, 29, p. 3659) carry out the reaction of the chiral organozinc halide (formed by reaction of methyl or ethyl bromoacetate with zinc and addition of (−)-sparteine) with the electrophile benzaldehyde at a temperature of 20° C., which did achieve high optical yields of 95±3% ee but only very low chemical yields of a maximum of 38±7%. In contrast, when the reaction is carried out by the process according to the invention at a temperature of less than 15° C., surprisingly, a very high chemical yield of 97% and at the same time a high optical yield of 89% ee are achieved (cf. Example 6).

In the process according to the invention, it is unimportant whether the reaction is effected by the addition of the aldehydes or imines of the general formula (2) to the mixture of the organozinc halide of the general formula (3) where Hal is in this case halozinc, and the N-auxiliary, or by the addition of the organozinc halide to the mixture of aldehydes or imines of the general formula (2) and the N-auxiliary, or by the addition of the mixture of organozinc halide and N-auxiliary to the aldehydes or imines of the general formula (2).

Preference is given to effecting the addition at temperatures of from −110 to +10° C., more preferably from −80 to 0° C., in particular from −40 to −10° C.

After the end of the addition of all constituents involved, the reaction is allowed to continue preferably for another from 30 min to 24 h, more preferably from 1 to 18 h, in particular from 2 to 10 h, in order to complete the reaction.

Excessive zinc metal may be removed by filtration. It is also possible to dissolve excess zinc in any acid used for hydrolyzing the reaction mixture.

After completed reaction, the reaction mixture is customarily hydrolyzed at temperatures of from −110 to +60° C., more preferably from −40 to +10° C., optionally after the addition of a water-immiscible organic solvent, preferably toluene, methylene chloride, ethyl acetate or tert-butyl methyl ether, by adding water, an aqueous acid or base to dissolve zinc compounds and zinc salts formed.

Alternatively, the reaction mixture may also be added to water, an aqueous acid or base.

Preferred bases are ammonia and organic amines, such as trialkylamines and alkanolamines.

Preferred acids are Bronsted acids, in particular strong acids such as boric acid, tetrafluoroboric acid, nitric acid, nitrous acid, phosphoric acid, phosphorous acid, hypophosphorous acid, sulfuric acid, sulfurous acid, peroxosulfuric acid, hydrochloric acid, hydrofluoric acid, hydroiodic acid, hydrobromic acid, perchloric acid, hexafluorophosphoric acid, benzenesulfonic acid, p-toluenesulfonic acid, methanesulfonic acid, trifluoromethanesulfonic acid and carboxylic acid, such as chloroacetic acid, trichloroacetic acid, acetic acid, acrylic acid, benzoic acid, trifluoroacetic acid, citronic acid, crotonic acid, formic acid, fumaric acid, maleic acid, malonic acid, gallic acid, itaconic acid, lactic acid, tartaric acid, oxalic acid, phthalic acid and succinic acid.

In particular, ammonia, hydrochloric acid, sulfuric acid, acetic acid or citric acid are used, preferably ammonia, hydrochloric acid, sulfuric acid and acetic acid. The acid or base may be used in concentrated form or in the form of a dilute aqueous solution.

Alternatively to the hydrolysis, it is possible to admix the reaction mixture, customarily at temperatures of from −110 to +100° C., preferably from −40 to +50° C., with an alkylating or arylating reagent, an acylating reagent or a silylating reagent, optionally in the presence of a solvent. The products of the general formula (1a) or (1b) alkylated, arylated, silylated or acylated in the 3-oxy- or 3-aminoposition obtained in this way may then be easily isolated after hydrolysis or optionally directly from the mixture, for example by distillation, extraction or crystallization.

Useful alkylating or arylating, acylating or silylating reagents are all suitable reagents well known to those skilled in the art from the prior art.

Preferred alkylating agents are methyl, ethyl, propyl, butyl or benzyl chloride, bromide or iodide.

Preferred arylating reagents are fluorobenzene, 1-fluoro-4-trifluoromethylbenzene, 1-fluoronaphthalene, chlorobenzene, 1-chloro-4-trifluoromethylbenzene or 1-chloronaphthalene, in particular 1-fluoronaphthalene or 1-fluoro-4-trifluoromethylbenzene.

Preferred acylating reagents are acetyl chloride or bromide and acetic anhydride, in particular acetic anhydride.

Preferred silylating reagents are trimethyl-, -ethyl-, -propyl- and -butylchlorosilane and tert-butyldimethylchlorosilane, in particular trimethylsilane.

When the reactive halogen compounds of the general formula (3) used are silyl compounds where Y=(C=O)—Z and Z=OSi($R^1$)$_3$ where $R^1$ may be as defined above and is in particular selected from the abovementioned preferred embodiments of $R^1$, subsequent hydrolysis under the abovementioned conditions provides carboxylic acids where Z is in this case OH.

The products of the general formula (1a) or (1b) obtained in this way may also finally be isolated from the organic phase of the reaction mixture by phase separation. They may be separated from the organic phase by known, customarily used methods such as extraction, distillation, crystallization or by means of chromatographic methods. In most cases, even the crude product obtained after removal of the solvent is of very high purity.

Optionally, crystalline compounds of the general formulae (1a) or (1b) are recrystallized for optional further enantiomeric enrichment. For recrystallization, preference is given to dissolving the reaction products in the form of their crude products in a suitable solvent and recrystallized, optionally by seeding with an enantiomerically pure compound.

As described at the outset, it has been found that the chiral N-auxiliary can be isolated as a zinc-containing solid in the workup of the reaction mixture and can be recovered therefrom in high yields. The workup may preferably be aqueous, acidic or alkaline, or be effected using a silylating, alkylating, arylating or acylating reagent, in particular under nonaqueous conditions with a silylating reagent.

The removal of the zinc-containing solid from the reaction mixture on the one hand allows the majority of the zinc to be removed from the reaction mixture, so that no zinc-containing solutions or other zinc-containing waste arise and, on the other hand, the N-auxiliary used can be recovered in high yields from the removed zinc-containing solid and regenerated.

In particular, when using (−)-sparteine as the-auxiliary, the recovery can be carried out in high yields, in particular when using a silylating reagent in the workup.

The simple and effective recovery of the chiral-auxiliary, in particular (−)-sparteine, makes the process according to the invention particularly economical.

The N-auxiliary, in particular (−)-sparteine, may be distillatively freed from impurities and purified before reuse. Particular preference is given to reusing sparteine without distillative purification.

It has proven useful to react the zinc with the reactive halogen compound of the general formula (3), the aldehyde or imine and the chiral N-auxiliary in a molar ratio of (1 to 3):(1 to 2):1:(0.1 to 2.5), in particular (1.1 to 1.7):(1 to 1.3):1:(0.1 to 1.5).

Zinc is generally used in the form of foil, ribbon, turnings, powder or dust, or in the form of zinc wool. The presence of other metals such as copper, silver or mercury is unnecessary. In particular, zinc is used in the form of commercially obtainable, commercially customary zinc powder or zinc dust, and preference is given to zinc of high purity of at least 99.995%, greater preference to zinc dust which is obtained from zinc having a purity of at least 99.995%.

To achieve high product yields and purities, it has proven advantageous to activate the zinc before addition of the reactive halogen compound of the general formula (3) or of the chiral N-auxiliary or mixture thereof. Suitable methods for zinc activation are existing methods which are customarily used and mentioned, for example, in the review of A. Furstner, *Synthesis* 1989, p. 571. It has proven useful to wash the zinc with acid, activate with iodine as described in EP-A-562 343 and activate using trimethylchlorosilane. Particular preference is given to activation using trimethylchlorosilane owing to the ease with which it is carried out, and the increased yields, product purities and selectivities and also the suppression of side reactions. G. Picotin, P. Miginiac, *J. Org. Chem.* 1987, 52, p. 4796 disclose the activation of zinc using trimethylchlorosilane in the solvent diethyl ether.

To activate zinc with trimethylchlorosilane, the zinc is initially charged to the solvent or solvent mixture, then trimethylchlorosilane is added and the mixture is heated to temperatures from 20 to 150° C., in particular from 30 to 120° C., preferably from 40 to 80° C. for from 10 min to 2 h, preferably from 5 to 45 min. It has proven useful to react the zinc with trimethylchlorosilane in a molar ratio of 1:(0.01 to 0.5), in particular 1:(0.05 to 0.3) with heating to the desired temperature.

To activate the reaction mixture, it is also possible to use additives such as compounds of copper, chromium, manganese, cobalt, bismuth, samarium, scandium, indium, titanium, cerium, tellurium, tin, lead, antimony, germanium, aluminum, magnesium, palladium, nickel and mercury, or optionally mixtures thereof.

The pressure range of the reaction is uncritical and may be varied within wide limits. The pressure is typically from 0.01 to 20 bar, but preference is given to carrying out the reaction under atmospheric pressure.

Preference is given to carrying out the reaction with inertization by protective gas, such as nitrogen or argon. The reaction may be carried out continuously or batchwise, preferably batchwise.

All of the abovementioned symbols of the abovementioned formulae are each defined independently of one another.

DETAILED DESCRIPTION OF THE PREFERRED EMBODIMENTS

In the examples which follow, unless otherwise stated, all amounts and percentages are based on weight, all pressures are 0.10 MPa (abs.) and all temperatures are 20° C.

EXAMPLE 1

Preparation of Methyl (S)-(−)-3-hydroxy-3-(2-thiophene)propionate

At room temperature, a three-neck flask equipped with a reflux condenser, internal thermometer, dropping funnel and stirrer under protective nitrogen gas was initially charged with 9 g of zinc dust (138 mmol) in 70 ml of tetrahydrofuran. After 2.3 ml of trimethylchlorosilane had been added, the mixture was heated to 60° C. for 15 min, and 20.4 g of methyl bromoacetate (134 mmol) were subsequently added dropwise undiluted at 45° C. within 7 min. The mixture was then stirred for 15 min and admixed with 20 ml of 1-methyl-2-pyrrolidone. After cooling to 0° C., 32.6 g of (−)-sparteine (139 mmol) were added undiluted, and the temperature rose to 8° C. After the clear mixture had been stirred at 40° C. for 10 min., it was cooled to 20° C. and 12.4 g of thiophene-2-carbaldehyde (111 mmol) were added undiluted. The clear reaction mixture was subsequently stirred at 20° C. for 8 h, then acidified at this temperature to a pH of 2 using 35 ml of 20% hydrochloric acid and stirred for 10 min, and the temperature of the mixture rose to 0° C. 150 ml of water were then added. Precipitated sparteine salt was filtered off with suction and washed twice with 40 ml of ethyl acetate each time (>80% of sparteine could be recovered). After removing the organic phase, the aqueous phase was extracted using 50 ml of ethyl acetate and the organic phase was subsequently removed. The organic phase was then stirred with 20 ml of concentrated ammonia solution at 10° C. for 10 min. After phase separation, the solvent was very substantially distilled off under reduced pressure and the residue was washed with 20 ml of water. After phase separation, drying and removal of solvent under reduced pressure, methyl (S)-(−)-3-hydroxy-3-(2-thiophene)propionate was obtained in a yield of 19.8 g (96% of theory) and a purity of >94% and 91% ee (HPLC) and a boiling point of 89° C. (0.6 mbar).

EXAMPLE 2

Preparation of Ethyl (S)-(−)-3-hydroxy-3-(2-thiophene)propionate

At room temperature, a three-neck flask equipped with a reflux condenser, internal thermometer, dropping funnel and stirrer under protective nitrogen gas was initially charged with 9 g of zinc dust (138 mmol) in 60 ml of tetrahydrofuran. After 2.3 ml of trimethylchlorosilane had been added, the mixture was heated to 60° C. for 15 min, and 22.4 g of ethyl bromoacetate (134 mmol) were subsequently added dropwise undiluted at 45° C. within 7 min. The mixture was then stirred for 15 min. After cooling to 0 C, 60 ml of dimethylformamide were added and subsequently 32.6 g of (−)-sparteine (139 mmol) were added undiluted, and the temperature rose to 8 C. After the clear mixture had been stirred at 10° C. for 10 min, it was cooled to 20° C. and 12.4 g of thiophene-2-carbaldehyde (111 mmol) were added undiluted. The clear reaction mixture was subsequently stirred at 20° C. for 8 h, then acidified at this temperature to a pH of 2 using 35 ml of 20% hydrochloric acid and stirred for 10 min, and the temperature of the mixture rose to 0° C. 150 ml of water were then added. Precipitated sparteine salt was filtered off with suction and washed twice with 40 ml of ethyl acetate each time (>80% of sparteine could be recovered). After removing the organic phase, the aqueous phase was extracted using 50 ml of ethyl acetate and the organic phase was subsequently removed. The organic phase was then stirred with 20 ml of concentrated ammonia solution at 10° C. for 10 min. After phase separation, drying and removal of solvent under reduced pressure, ethyl (S)-(−)-3-hydroxy-3-(2-thiophene)propionate was obtained in a yield of 20.9 g (94% of theory) and a purity of >94% and 89% ee (HPLC).

EXAMPLE 3

Preparation of Methyl (S)-(−)-3-(2-thiophene)-3-trimethyl-siloxypropionate

At room temperature, a three-neck flask equipped with a reflux condenser, internal thermometer, dropping funnel and stirrer under protective nitrogen gas was initially charged with 5 g of zinc dust (77 mmol) in 30 ml of tetrahydrofuran. After 1.2 ml of trimethylchlorosilane had been added, the mixture was heated to 55° C. for 15 min, and 10.9 g of methyl bromoacetate (71 mmol) were subsequently added dropwise undiluted while refluxing at 40° C. within 7 min. The mixture was then stirred for 10 min. After cooling to 20° C., 30 ml of tetrahydrofuran were added and 17 g of (−)-sparteine (72 mmol) were subsequently added undiluted at 0° C., and the temperature rose to 10° C. The mixture was cooled to −15° C. and 6.6 g of thiophene-2-carbaldehyde (60 mmol) were added undiluted. The reaction mixture was subsequently stirred at −15° C. for 20 h, then admixed at this temperature with 8 g of trimethylchlorosilane (74 mmol), and the temperature of the mixture rose to 10° C. and a precipitate formed. The mixture was subsequently stirred at 20° C. for 1 h, half of the organic solvent was distilled off under reduced pressure, and the residue was admixed with 70 ml of pentane, stirred for 30 min and cooled to 0° C. Precipitated sparteine salt was filtered off with suction and washed twice with 50 ml of pentane each time (>90% of the sparteine could be recovered). The organic product phase was washed with 5 ml of saturated sodium hydrogencarbonate solution. After phase separation, drying and removal of solvent under reduced pressure, methyl (S)-(−)-3-(2-thiophene)-3-trimethylsiloxypropionate was obtained in a yield of 15 g (98% of theory) and a purity of >95% and 89% ee (HPLC). Optical rotation: αD =−54.3 (20° C., methylene chloride, c=4); boiling point: 70–71° C. (0.04 mbar).

EXAMPLE 4

Preparation of Methyl (S)-(−)-3-methoxy-3-(2-thiophene)propionate

At room temperature, a three-neck flask equipped with a reflux condenser, internal thermometer, dropping funnel and stirrer under protective nitrogen gas was initially charged with 5 g of zinc dust (77 mmol) in 30 ml of tetrahydrofuran. After 1.2 ml of trimethylchlorosilane had been added, the mixture was heated to 55° C. for 15 min, and 10.9 g of methyl bromoacetate (71 mmol) were subsequently added dropwise undiluted at 45° C. within 7 min. The mixture was then stirred for 10 min. After cooling to 20° C., 30 ml of tetrahydrofuran were added and 17 g of (−)-sparteine (72 mmol) were subsequently added undiluted at 0° C., and the temperature rose to 10° C. The mixture was cooled to −15° C. and 6.6 g of thiophene-2-carbaldehyde (60 mmol) were added undiluted. The reaction mixture was subsequently stirred at 15 C for 20 h, then admixed at this temperature with 10.5 g of methyl iodide (74 mmol), and the temperature of the mixture rose to 0 C. The mixture was subsequently stirred at 20 C for 1 h, half of the organic solvent was distilled off under reduced pressure, and cooled to 0° C. Precipitated sparteine salt was filtered off with suction and washed twice with 50 ml of pentane each time (>90% of the sparteine could be recovered). The organic product phase was washed with 5 ml of saturated sodium hydrogencarbonate solution. After phase separation, drying and removal of solvent under reduced pressure, methyl (S)-(−)-3-methoxy-3-(2-thiophene)propionate was obtained in a yield of 11.1 g (92% of theory) and 89% ee (HPLC).

EXAMPLE 5

Preparation of Methyl (S)-(−)-3-acetoxy-3-(2-thiophene)propionate

At room temperature, a three-neck flask equipped with a reflux condenser, internal thermometer, dropping funnel and stirrer under protective nitrogen gas was initially charged with 5 g of zinc dust (77 mmol) in 30 ml of tetrahydrofuran. After 1.2 ml of trimethylchlorosilane had been added, the mixture was heated to 55° C. for 15 min, and 10.9 g of methyl bromoacetate (71 mmol) were subsequently added dropwise undiluted at 45° C. within 7 min. The mixture was then stirred for 10 min. After cooling to 20° C., 30 ml of tetrahydrofuran were added and 17 g of (−)-sparteine (72 mmol) were subsequently added undiluted at 0° C., and the temperature rose to 10 C. The mixture was cooled to 15° C. and 6.6 g of thiophene-2-carbaldehyde (60 mmol) were added undiluted. The reaction mixture was subsequently stirred at 15° C. for 20 h, then admixed at this temperature with 5.8 g of acetyl chloride (74 mmol), and the temperature of the mixture rose to 10 C. The mixture was subsequently stirred at 20 C for 1 h, half of the organic solvent was distilled off under reduced pressure, and the residue was admixed with 70 ml of pentane, stirred for 30 min and cooled to 0 C. Precipitated sparteine salt was filtered off with suction and washed twice with 50 ml of pentane each time (>90% of the sparteine could be recovered). The organic product phase was washed with 5 ml of saturated sodium hydrogencarbonate solution. After phase separation, drying and removal of solvent under reduced pressure, methyl (S)-(−)-3-acetoxy-3-(2-thiophene)propionate was obtained in a yield of 13.1 g (93% of theory) and 89% ee (HPLC).

EXAMPLE 6

Preparation of Methyl (S)-(−)-3-hydroxy-3-phenylpropionate

At room temperature, a three-neck flask equipped with a reflux condenser, internal thermometer, dropping funnel and stirrer under protective nitrogen gas was initially charged with 5 g of zinc dust (77 mmol) in 30 ml of tetrahydrofuran. After 1.2 ml of trimethylchlorosilane had been added, the mixture was heated to 55 C for 15 min, and 10.9 g of methyl bromoacetate (71 mmol) were subsequently added dropwise undiluted while refluxing at 45° C. within 7 min. The mixture was then stirred for 10 min. After cooling to 10 C, 30 ml of tetrahydrofuran were added and 17 g of (−)-sparteine (72 mmol) were subsequently added undiluted at 0 C, and the temperature rose to 5 C. The mixture was cooled to 15 C and 6.4 g of benzaldehyde (60 mmol) were added undiluted. The reaction mixture was subsequently stirred at 15 C for 20 h, then acidified at this temperature with 35 ml of 20% hydrochloric acid to a pH of 3 and stirred for 10 min, and the temperature of the mixture rose to 0 C. 150 ml of water were then added. Precipitated sparteine salt was filtered off with suction and washed twice with 40 ml of ethyl acetate each time. After removing the organic phase, the aqueous phase was extracted with 50 ml of ethyl acetate and the organic phase was subsequently removed. The organic phase was then stirred with 20 ml of concentrated ammonia solution at −10° C. for 5 min. After phase separation, drying and removal of solvent under reduced pressure, methyl (S)-(−)-3-hydroxy-3-phenylpropionate was obtained in a yield of 10.5 g (97% of theory) and a purity of >95% and 89% ee (HPLC).

In a similar manner, the following compounds were prepared:

| Substrate | Product | Yield [% of theory] | ee [%] |
|---|---|---|---|
| 2-fluorobenzaldehyde | methyl (S)-3-(2-fluorophenyl)-3-hydroxypropionate | 92[a] | 87 |
| 2-chlorobenzaldehyde | methyl (S)-3-(2-chlorophenyl)-3-hydroxypropionate | 96[a] | 89 |
| 2-bromobenzaldehyde | methyl (S)-3-(2-bromophenyl)-3-hydroxypropionate | 97[a] | 88 |
| 3-bromobenzaldehyde | methyl (S)-3-(3-bromophenyl)-3-hydroxypropionate | 95[a] | 89 |
| 2-nitrobenzaldehyde | methyl (S)-3-(2-nitrophenyl)-3-hydroxypropionate | 95[a] | 87 |
| 4-nitrobenzaldehyde | methyl (S)-3-(4-nitrophenyl)-3-hydroxypropionate | 92[a] | 88 |
| 2-methoxybenzaldehyde | methyl (S)-3-(2-methoxyphenyl)-3-hydroxypropionate | 96 | 90 |

-continued
| Substrate | Product | Yield [% of theory] | ee [%] |
|---|---|---|---|
| 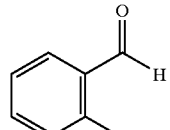 | 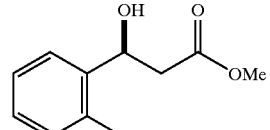 | 94 | 91 |
| 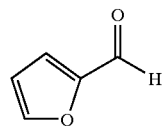 | 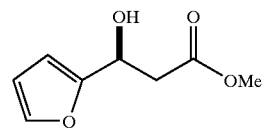 | 94[b] | 89 |
| 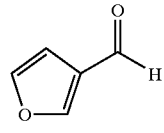 | 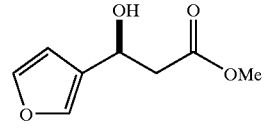 | 90[b] | 89 |
| 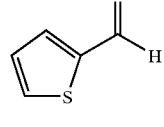 | 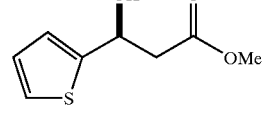 | 97 | 89 |
| 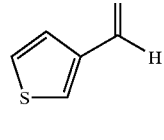 | 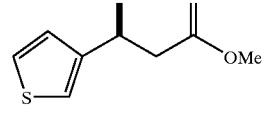 | 95 | 89 |
| 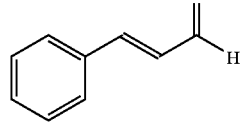 | 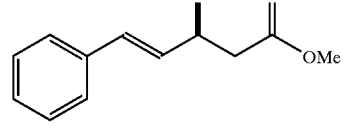 | 91[a] | 85 |
| 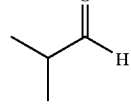 | 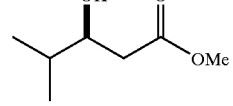 | 87[a,c] | 87 |
| 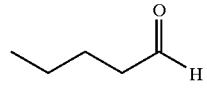 | 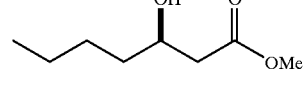 | 90[a,d] | 89 |
|  | 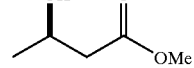 | 86[a,e] | 87 |
| 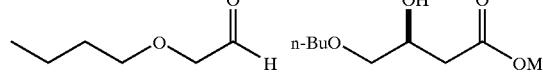 | 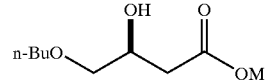 | 90 | 88 |
[a] The reaction with the electrophile was effected at −25° C.
[b] The mixture of organozinc compound and (−)-sparteine was added to furfural.
[c] Boiling point: 35° C. (1 mbar).
[d] Boiling point: 46° C. (1 mbar).
[e] Boiling point: 71° C. (30 mbar).

What is claimed is:

1. A process for preparing compounds of the general formula (1a) or (1b)

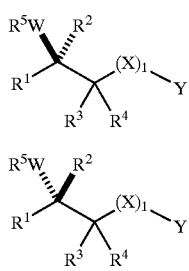

where
- $R^1$ and $R^2$ are each independently hydrogen or an optionally halogen- or cyano-substituted $C_1$–$C_{30}$-hydrocarbon radical in which one or more, nonadjacent methylene units may be replaced by —O—, —CO—, —COO—, —OCO—, or —OCOO—, —S— or —NR$^x$— groups, and in which one or more methine units may be replaced by —N= or —P= groups,
- $R^3$ and $R^4$ are each independently hydrogen, halogen, or an optionally halogen-substituted or cyano-substituted $C_1$–$C_{30}$-hydrocarbon radical in which one or more, nonadjacent methylene units may be replaced by —O—, —CO—, —COO—, —OCO—, or —OCOO—, —S— or —NRx— groups, and in which one or more methine units may be replaced by —N= or —P= groups,
- $R^x$ is hydrogen or an optionally halogen-substituted $C_1$–$C_{30}$-hydrocarbon radical in which one or more, nonadjacent methylene units may be replaced by —O—, —CO—, —COO—, —OCO—, or —OCOO—, —S—, —NH— or —N—C1–C20-alkyl groups, and in which one or more methine units may be replaced by —N= or —P= groups, and
- X is selected from

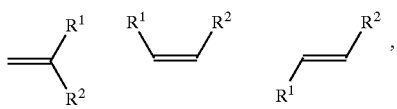

- l is an integer having the value 0 or 1,
- W may be O or $NR^6$,
- $R^5$ may be hydrogen or an alkyl, aryl, acyl or silyl group and
- $R^6$ may be hydrogen, Si $(R^1)_3$ or an optionally halogen- or cyano-substituted $C_1$–$C_{30}$-hydrocarbon radical in which one or more, nonadjacent methylene units may be replaced by —O—, —CO—, —COO—, —OCO—, or —OCOO—, —S—, —SO—, —SO2-, —P($R^1$)—, —P(O$R^1$)—, —PO($R^1$)—, —PO(O$R^1$)—, or —NR$_x$— groups, and in which one or more methine units may be replaced by —N= or —P= groups,
- Y is CN, (C=O)—Z, (SO$_2$)—Z, (P=O)(—Z)$_2$ or an aromatic radical where one or more methine units in the ring may be replaced by —N= or —P= groups and the ring may be of the heteroatoms —O—, —S— or —NH—, and where the aromatic ring is optionally halogen- or cyano-substituted or substituted by $C_1$–$C_{30}$-hydrocarbon radicals in which one or more, nonadjacent methylene units may be replaced by —O—, —CO—, —COO—, —OCO—, or —OCOO—, —S— or —NR$^x$-groups, and
- Z is an optionally halogen-substituted $C_1$–$C_{30}$-hydrocarbon radical in which one or more, nonadjacent methylene units may be replaced by —O—, —CO—, —COO—, —OCO—, or —OCOO—, —S—, or —NR$^x$— groups, and in which one or more methine units may be replaced by —N= or —P= groups, or is OH, $OR^1$, $OSi(R^1)_3$, $NHR^1$ or $NR^1R^2$, which comprises reacting aldehydes or imines of the general formula (2)

$$R^1R^2C=W \qquad (2)$$

at a temperature of less than 15° C.
in the presence of a chiral, enantiomerically pure auxiliary having at least two nitrogen donors and at least one cyclic group, with the proviso that protons present have a pKa of greater than 18
with an organozinc halide which is obtained from zinc and a reactive halogen compound of the general formula (3)

$$\text{Hal-}R^3R^4C—(X)_l—Y \qquad (3)$$

where
- Hal is chlorine, bromine or iodine,
- and subsequently adding water, acid or base, or a reagent selected from the group consisting of an alkylating reagent, an arylating reagent, an acylating reagent and a silylating reagent.

2. The process as claimed in claim 1, wherein the reaction is carried out in a solvent selected from the group consisting of the cyclic ethers, di- or oligoethers having at least one ethylene bridge, carboxylic esters, amines, amides, polar aprotic solvents, halogenated hydrocarbons, and solvent mixtures thereof.

3. The process as claimed in claim 1, wherein the chiral, enantiomerically pure auxiliary is (–)-sparteine.

4. The process as claimed in claim 1, wherein a Reformatsky reagent required for the reaction is prepared by initially charging zinc in a solvent or solvent mixture,
subsequently adding the reactive halogen compound, optionally dissolved in a solvent, and
finally adding the chiral, enantiomerically pure auxiliary, optionally dissolved in a solvent.

5. The process as claimed in claim 4, wherein the organozinc halides are prepared at from 25° to 50° C.

6. The process as claimed in claim 4, wherein the chiral, enantiomerically pure auxiliary is added to the organozinc halides at from –30° C. to +30° C.

7. The process as claimed in claim 1, wherein the aldehydes or imines are reacted with the organozinc halide in the presence of the chiral, enantiomerically pure auxiliary at a temperature of from –10° C. to –40° C.

8. The process as claimed in claim 1, wherein the zinc is removed from a reaction solution in a form of a solid containing zinc and the chiral, enantiomerically pure auxiliary.

9. The process as claimed in claim 8, wherein the chiral, enantiomerically pure auxiliary is recovered from the solid.

10. The process as claimed in claim 1, wherein the reactive halogen compound used is an α-bromoacetic ester.

* * * * *